United States Patent [19]

Sanuki

[11] Patent Number: 5,447,691

[45] Date of Patent: * Sep. 5, 1995

[54] LIQUID SUPPLYING DEVICE FOR USE IN PHYSICAL AND CHEMICAL APPARATUS

[75] Inventor: Sannosuke Sanuki, Hamuramachi, Japan

[73] Assignee: Sanuki Kogyo Co., Ltd., Tokyo, Japan

[*] Notice: The portion of the term of this patent subsequent to May 3, 2011 has been disclaimed.

[21] Appl. No.: 153,913

[22] Filed: Nov. 17, 1993

Related U.S. Application Data

[63] Continuation of Ser. No. 906,868, Jul. 1, 1992, Pat. No. 5,308,583.

[30] Foreign Application Priority Data

Jul. 4, 1991 [JP] Japan .................................. 3-190588

[51] Int. Cl.$^6$ .............................................. B01L 3/02
[52] U.S. Cl. .............................. 422/100; 422/103; 137/567; 137/597
[58] Field of Search ................ 422/100, 103; 137/567, 137/597

[56] References Cited

U.S. PATENT DOCUMENTS

| | | | |
|---|---|---|---|
| 4,710,355 | 12/1987 | Ushikubo | 422/100 |
| 5,096,670 | 3/1992 | Harris et al. | 422/65 |

*Primary Examiner*—James C. Housel
*Assistant Examiner*—Rachel Heather Freed
*Attorney, Agent, or Firm*—Armstrong, Westerman, Hattori, McLeland & Naughton

[57] ABSTRACT

A liquid supplying device has liquid supplying piston pumps driven by turns for drawing up liquids contained in chemical vessels through liquid intake passages and sending out the liquids to an analyzer or other inspection apparatus through liquid outlet passages. The liquid intake and outlet passages have change-over valves controlled by an automatic sequence controller so as to send out alternately the liquids in the properly mixed state to the analyzer without pulsation of flow.

1 Claim, 5 Drawing Sheets

LIQUID SUPPLYING DEVICE FOR USE IN PHYSICAL AND CHEMICAL APPARATUS

This is a continuation of application Ser. No. 07/906,868, filed Jul. 1, 1992, now U.S. Pat. No. 5,308,583.

BACKGROUND OF THE INVENTION

1. Field of the Invention

This invention relates to a liquid supplying device for supplying quantitatively various kinds of liquids such as sampler solutions, chemical reagents and other chemicals to a physical and chemical apparatus such as a liquid gas-chromatograph and or reaction analyzers.

2. Description of the Prior Art

In a liquid supplying device for use in physical and chemical apparatus, there has been generally used at least one proportioning pump such as a plunger pump, diaphragm pump and tubing pump.

The plunger pump has a liquid chamber defined between paired check valves for allowing liquid to pass in one direction and a plunger which moves to and fro within the liquid chamber so as to produce a unidirectional flow of the liquid. The diaphragm pump utilizes a diaphragm as a pressure generating means. As the check valve used in a pump of this type, there are a flap valve and a ball valve, for example.

The tubing pump produces a flow of liquid by utilization of succession of contraction waves on an elastic tube, the tube being repeatedly squeezed in one direction by means of a plurality of squeezing members operated by cams.

As conventional liquid supplying devices of the types other than the successively operated pumps as described above, there have been known a pump having a change-over valve for alternately switching liquid intake and outlet passages to each other so as to send out liquid introduced into a pump cylinder, and a pump having solenoid valves disposed respectively on liquid intake and outlet passages in place of the change-over valve mentioned above.

The aforenoted conventional liquid supplying devices using a plunger pump or diaphragm pump are suitable for supplying a small quantity of liquid, but requires at least one check valve. The use of such a check valve for controlling the flow of liquid in the liquid supplying device of this type entails a disadvantage such that it may possibly permit air bubbles to cling thereto so much as to decrease the amount of liquid being supplied. the operation of the valve may become unstable and further the inner pressure of the liquid flowing therethrough may vary with time in accordance with the change in size of the air bubbles resultantly produced, i.e. the so-called drift phenomenon in supplying liquid which causes the valve to be deactivated.

Since the check valve used in the pump is not operated at a constant speed with the pressure of the liquid supplied, the relation between the pressure and quantity of the supplied liquid cannot be maintained constant. This may disadvantageously lead to error in the quantity of the supplied liquid.

The tubing pump as noted above has a complicated mechanism for squeezing the elastic tube. Furthermore, this pump has problems such as inferiority in durability, pressure resistance and chemical resistance, and generation of pulsation flow of the liquid being sent out.

On the other hand, the liquid supplying devices using the change-over valves or other valves can solve the problems such as generation of air bubbles and inferiority in durability and pressure resistance as touched upon above, but cannot automatically control the momentum in one stroke of a piston used therein and the variation in operating rate according to a prescribed program. Therefore, the conventional liquid supplying devices of this type cannot be applied for the purpose of automatically pouring a given chemical reagent in a gas chromatograph, or combining a reagent and a reactant chemical to be poured to analyzers of various types.

SUMMARY OF THE INVENTION SUMMARY

In the light of the drawbacks suffered by the conventional liquid supplying devices as described above, this invention has an object to provide a liquid supplying device for use in physical and chemical apparatus which is of automatically supplying various kinds of liquids at an arbitrary flowing speed without generating pulsation flow of the liquid and air bubbles and without leading to error in the quantity of the liquid sent out, and having excellent durability, pressure resistance and chemical resistance.

To attain the object described above according to the present invention, there is provided a liquid supplying device for use in physical and chemical apparatus, which comprises at least one liquid supplying piston pump having a cylinder connected to liquid intake passages and at least one liquid outlet passage through respective change-over valves, a piston which moves to and fro within the cylinder, and a driving mechanism for operating the piston, and an automatic controller for the driving mechanism.

Liquids such as a chemical reagent and other chemicals are alternately introduced into and sent out from the cylinder by driving the piston pump under the control of the automatic controller. The liquids sent out of the cylinder are intermittently fed little by little to an analyzer or other inspection apparatus through the liquid outlet passage. The liquids can flow suitably in strata through the liquid outlet passage. By operating the piston to move to and fro within the cylinder at a regular operating rate, the liquids flow constantly without causing pulsation.

By using three piston pumps, each connected to reagent and reactant vessels through a change-over valve, liquids such as a reagent and other chemicals can be effectively sent out to the liquid outlet passages.

BRIEF DESCRIPTION OF THE DRAWINGS

Other objects and features of the present invention will be hereinafter explained in detail with reference to the accompanying drawings, wherein.

DESCRIPTION OF THE PREFERRED EMBODIMENT

Figure 1:
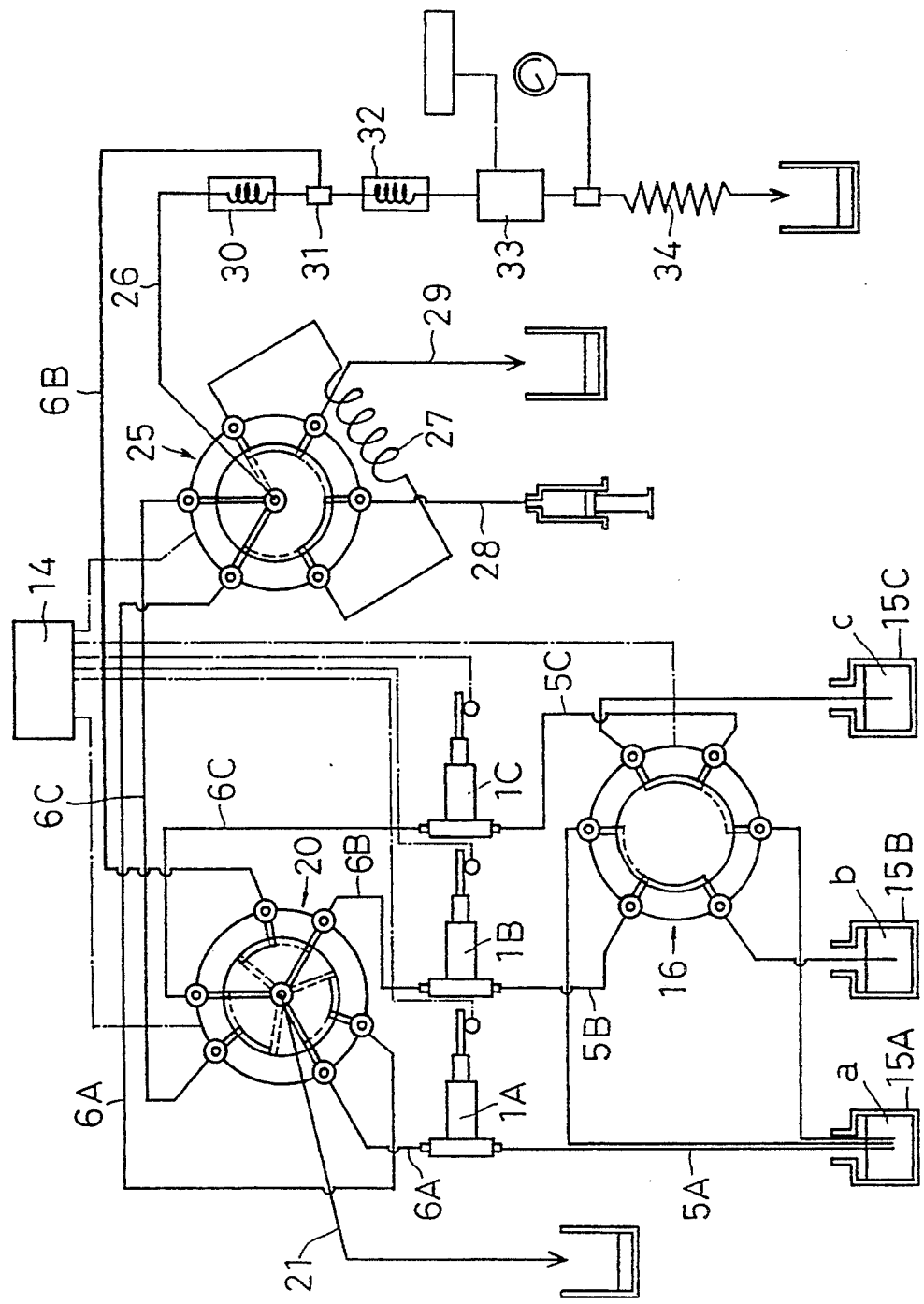
FIGS. 1 through 4 are flow diagrams of one embodiment of the liquid supplying device according to a present invention, showing the processes in which three kinds of liquids are supplied to an analyzer and then combined uniformly.

The present invention will become more fully understood from the detailed description given hereinbelow and the accompanying drawings which are given by way of illustration only, and thus are not limitative of the present invention.

FIGS. 1 through 4 show one embodiment of the present invention which is applied to a flow-injection device for supplying and combining three kinds of liquids. In the drawings, reference numerals 1A, 1B and 1C denote identical pumps.

Figure 5:
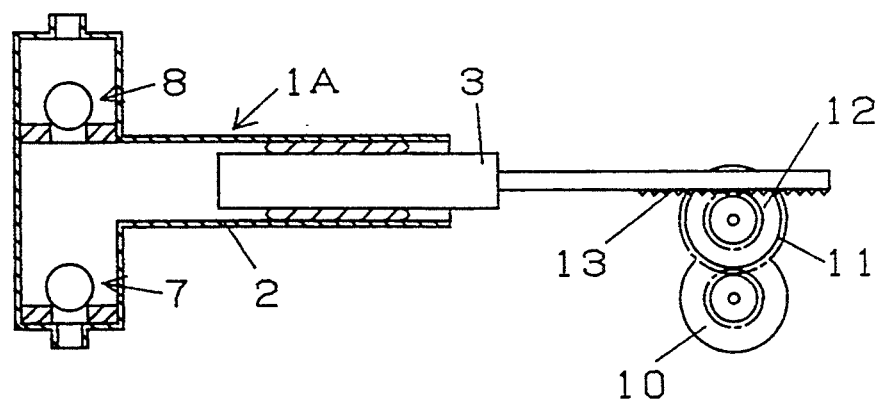
FIG. 5 is a schematic view showing a pump used in the liquid supplying device of this invention.

As shown in FIG. 5, the piston pump 1A has a cylinder 2, a piston 3 movable to and fro within the cylinder 2, and a driving mechanism 4 for operating the piston 3. The piston pumps 1A is connected to a intake passages through check valve 7 and to liquid outlet through check valve 8.

The driving mechanism of piston pump 1A has a pulse motor 10, reduction gears 11 and 12, and a rack 13, and is controlled by a sequence controller 14. Turning back to FIG. 1, piston pumps 1A-1C are connected to liquid intake passages 5A, 5B and 5C, on one side and to outlet passages 6A, 6B and 6C, respectively, on the other side.

The liquid intake passage 5A of the pump 1A is connected to a first chemical vessel 15A. The liquid intake passage 5B of the pump 1B is selectively connected to either the first chemical vessel 15A or a second chemical vessel 15B through a change-over valve 16. Also, the liquid intake passage 5C of the pump 1C is selectively connected to either the first chemical vessel 15A or a third chemical vessel 15C through the change-over valve 16. The change-over valve 16 assumes its first position for connecting the liquid intake passages 5B and 5C to the first chemical vessel 15A as indicated by the dashed line in FIG. 1. In the second position of the change-over valve 16, the liquid intake passages 5B and 5C are connected to the second and third chemical vessels 15B and 15C as shown in FIG. 2.

In this embodiment, the first chemical vessel 15A contains a carrier solution (a), the second chemical vessel 15B contains a first chemical reagent (b), and the third chemical vessel 15C contains a second chemical reagent (c).

In the liquid outlet passages 6A, 6B and 6C, a liquid discharging change-over valve 20 is disposed. To the center port of the change-over valve 20, there is connected a common drain passage 21 through which the liquids sent via the liquid outlet passages 6A, 6B and 6C are discharged when the change-over valve 20 assumes its first position as shown in FIG. 2. In the second position of the change-over valve 20, the liquid outlet passages 6A, 6B and 6C communicate with a passage 26 leading to an analyzer or other inspection apparatus.

In the liquid outlet passages 6A and 6C extending from the liquid discharging change-over valve 20, there is disposed a two-liquid mixing valve 25 for selectively passing not only the liquids but also a sampler liquid as described later. The mixing valve 25 has at its center a port leading to a reaction detecting passage 26. The mixing valve 25 permits, when assuming its first position shown in FIG. 3, the liquid outlet passages 6A and 6C to be connected to the reaction detecting passage 26, and simultaneously, forms a path from a sampler intake passage 28 to a sampler outlet passage 29 via a sampler coil passage 27. In the second position of the mixing valve 25 as shown in FIG. 4, the first liquid outlet passage 6A communicates with the reaction detecting passage 26 via the sampler coil passage 27, and the third liquid outlet passage 6C communicates with the reaction detecting passage 26.

The reaction detecting passage 26 is connected, in order, with a first reactor 30, a branch pipe 31 for introducing the reactant chemical, a second reactor 32, a detector 33 composed of a flow cell, and a resistor 34. To the branch pipe 31 is connected the second liquid outlet passage 6B.

The change-over valves 16 and 20 and mixing valve 25 are automatically controlled by a sequence controller 14 similarly to the driving mechanism 4.

Next, the operation of the aforementioned liquid supplying device will be described.

Figure 2:
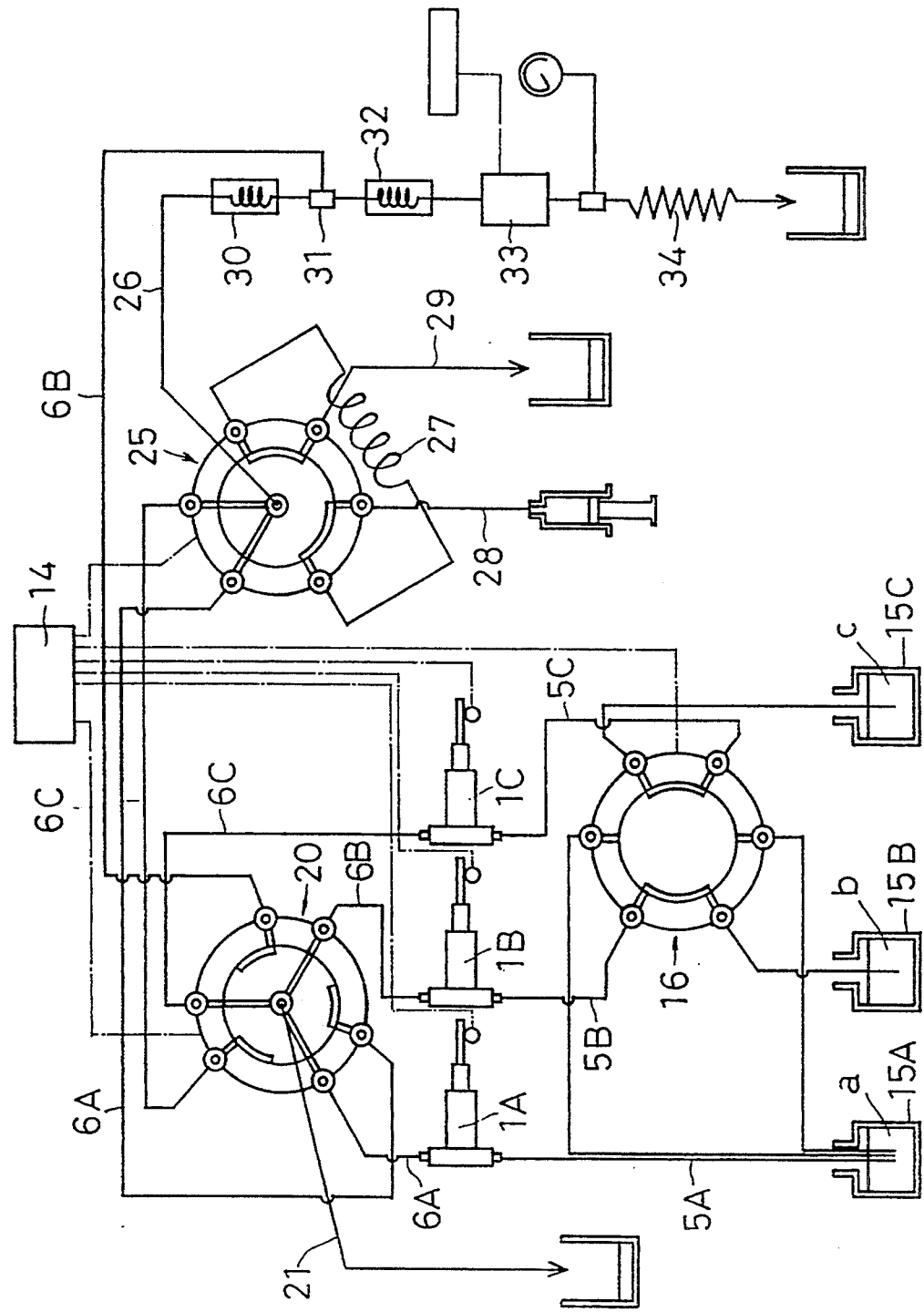

At the outset, in a preliminary process in which the liquid supplying device is at rest, the change-over valve 20 assumes its first position and the change-over valve 16 assumes its second position as shown in FIG. 1, so that all the passages are filled with the carrier solution (a), while permitting the carrier solution (a) to flow out through the drain passage 21. Then, by turning the change-over valve 16 to its second position as shown in FIG. 2, the liquid intake passages 5B and 5C are connected to the chemical vessels 15B and 15C, and at the same time, the pumps 1A to 1C are driven in turn by reciprocating the pistons 3 incorporated therein, thereby fill the passages 5B, 5C, 6B and 6C with the respective reactant chemicals (b) and (c).

Figure 3:
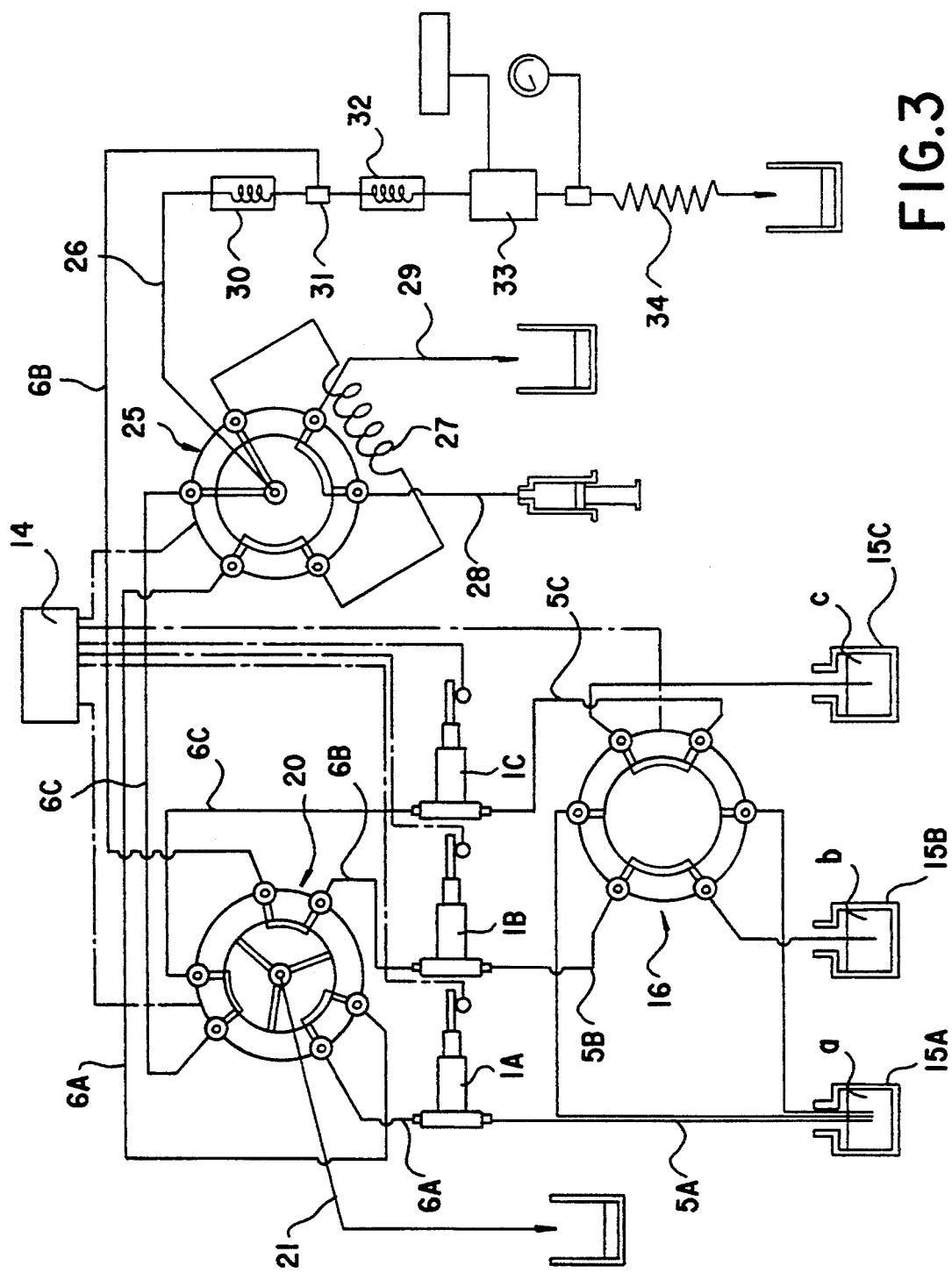
Figure 4:
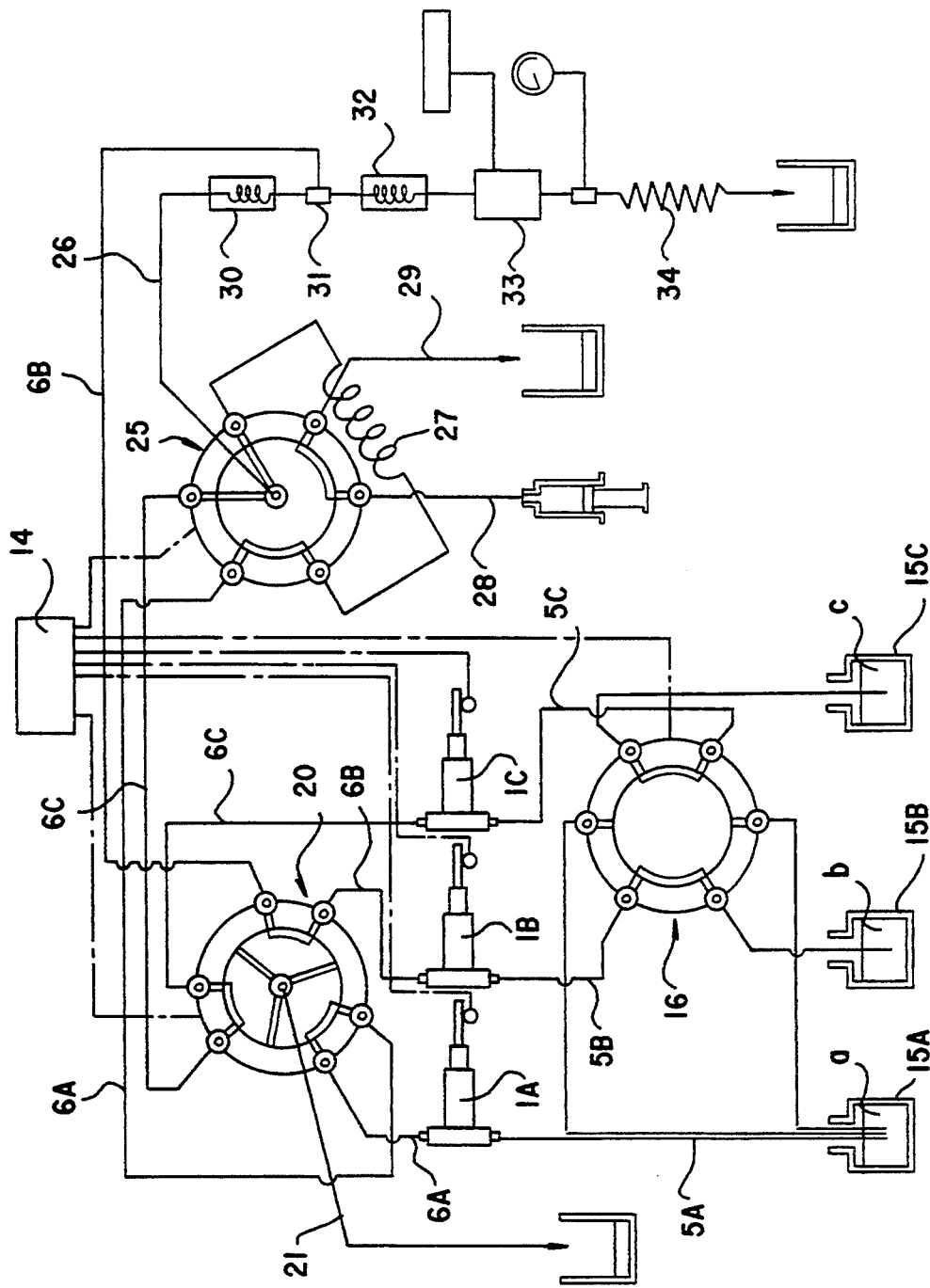

Thereafter, by turning the change-over valve 20 to its second position as shown in FIG. 3, the complete outlet passages 6A–6C from the pumps 1A–1C to the analyzer and valve 25 are formed. In this state, the two-liquid mixing valve is in its first position to permit both the outlet passages 6A and 6C to communicate with the reaction detecting passage 26. Then, the piston pumps 1A to 1C are continuously driven by turns to send out the carrier solution (a) and reactant chemicals (b) and (c).

The ratio at the carrier solution (a) and reactant chemicals (b) and (c) are mixed is made constant by continuously reciprocating the pistons within the pumps 1A to 1C with a small stroke. It is preferable that the amount of the solution discharged from each pump per one stroke of the piston is set to be as little as several micro liters, and the piston pumps are driven in turn and controlled so that only one of the pistons is operated to send out the liquid when the other pistons are at rest, thereby to send out the liquids alternately. Thus, the mixture solution obtained beyond the branch pipe 31 can flow without pulsation.

After filling the reaction detecting passage 26 with the carrier solution (a) and reactant chemicals (b) and (c), the two-liquid mixing valve 25 is turned to its second position as shown in FIG. 4 to cause the carrier solution (a) to send out the sampler solution with which the sampler coil passage 27 is filled in advance. As a result, the sampler solution sent out from the passage 27 is mixed with the reactant chemical (c) at the entrance of the reaction detecting passage 26. The mixture thus obtained is sent to the first reactor 30 and further mixed with the reactant chemical (b) in the branch pipe 31. Then, the mixture is introduced into the detector 33 via the second reactor 32.

Figure 6:
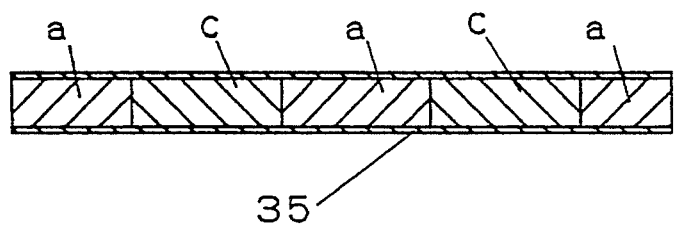
FIG. 6 is an explanatory view showing the first stage of supplying two kinds of liquids through a liquid outlet passage.
Figure 7:
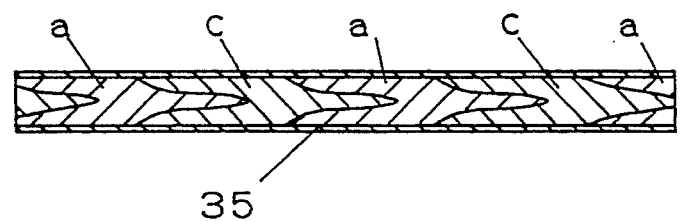
FIG. 7 is an explanatory view showing the middle stage of supplying two kinds of liquids through a liquid outlet passage.

In the manner described above, one reaction detecting process is completed. Immediately after the liquids are introduced into the passage 35 in the final stage, the liquids are mixed in such a state that the liquids (a) and (c) flow in strata as shown in FIG. 6. Thereafter, the liquids bring about difference in flowing velocity between the axial center portion and the circumferential portion being in contact with the inner wall of the passage 35 due to contact resistance, as shown in FIG. 7.

After the reaction detecting process is accomplished in the manner noted above, all the passages in the liquid supplying device are filled with a rinsing solution and the carrier solution in a post-treatment process. That is, in this post-treatment process, both of the change-over valves 16 and 20 are turned to their first positions as shown in FIG. 1 so as to connect all the liquid intake passages 5A–5C to the chemical vessel 15A and all the liquid outlet passages 6A–6C are connected to the drain passage 21, while reciprocating the pistons 3 in the pumps 1A–1C with a large stroke to rinse the interiors of the passages and fill the passages with the carrier solution (a). Successively, the liquid discharging change-over valve 20 is turned to its second position as shown in FIG. 3 so as to allow the carrier solution to flow into the liquid outlet passages 6A–6C. At that time, the two-liquid mixing valve 25 is turned as to flow cause the carrier solution (a) into the sampler coil passage 27 and reaction detecting passage 26 for rinsing these passages. Finally, these passages are entirely filled with the carrier solution (a).

Though the flow injection device for mixing two kinds of liquids is used in the foregoing embodiment, the liquid supplying device of this invention may be applied to a reaction analyzing device in which two kinds of liquids are mixed. Also in the embodiment described above, the three piston pumps 1A–1C are preferably used, but even only one piston pump suffices for the liquid supplying device of this invention. That is to say, the number of the piston pumps used in the liquid supplying device of this invention is not specifically limited.

As is apparent from the foregoing description, since the liquid supplying device according to the present invention has at least one piston pump which is operated by the driving mechanism under the control of the automatic controller, various kinds of liquids such as sampler solutions, chemical reagents and other chemicals can be supplied quantitatively without generating pulsation flow and air bubbles as caused in the prior art plunger pump and diaphragm pump. In addition, the liquid supplying device of the present invention can mix the liquids with high efficiency and excels in durability, pressure resistance and chemical resistance.

Although the invention has been described in its preferred form with a certain degree of particularity, it is understood that the present disclosure of the preferred form may be changed in the details of construction and the combination and arrangement of parts may be resorted to without departing from the spirit and the scope of the invention as hereinafter claimed.

What is claimed is:

1. A liquid supplying device for use in physical and chemical apparatus, comprising:

liquid supplying piston pumps each having a cylinder connected to a liquid intake passage and a liquid outlet passage through respective check valves, a piston which moves to and from within said cylinder, and a driving mechanism for operating said piston, said liquid intake passages being connected to respective chemical vessels containing liquids, said liquid outlet passages being connected to the physical and chemical apparatus, a change-over valve disposed in said liquid intake passages of said piston pumps, a liquid discharging change-over valve disposed in said liquid outlet passages of said piston pumps, and an automatic controller for controlling said driving mechanisms, change-over valve and liquid discharging change-over valve, said automatic controller operating each of said driving mechanisms for the supplying piston pumps so as to fill the cylinder with the liquid from said liquid intake passage in one suction stroke of the piston pumps, and so as to, during one complete discharge stroke of the piston pumps, intermittently discharge an incremental amount of the liquid to said liquid outlet passage, wherein said incremental amount is several microliters, said automatic controller operating said piston pumps by turns such that one of the piston pumps is operating to send out the liquid from a respective one of the chemical vessels and the remaining piston pumps are at rest in order to alternately send out the liquids from said chemical vessels to said apparatus.

* * * * *